United States Patent
Varner

[11] Patent Number: 6,105,577
[45] Date of Patent: Aug. 22, 2000

[54] ADVANCED TRACHEOSTOMY TUBE AND ORAL ENDOTRACHEAL TUBE HOLDER

[76] Inventor: Scott H. Varner, 1218 Rembrandt Cir., Charlotte, N.C. 21211

[21] Appl. No.: 09/181,506

[22] Filed: Oct. 28, 1998

[51] Int. Cl.⁷ .................................................. A61M 16/00
[52] U.S. Cl. .................................. 128/207.17; 128/207.14
[58] Field of Search ......................... 128/207.17, 207.15, 128/207.14, 207.16, 207.18, 200.26, DIG. 26, 912, 202.27, 911; 623/9; 604/265

[56] References Cited

U.S. PATENT DOCUMENTS

| | | | |
|---|---|---|---|
| 3,286,713 | 11/1966 | Kurtz et al. | 128/DIG. 26 |
| 3,422,817 | 1/1969 | Miskin et al. | 128/DIG. 26 |
| 3,683,911 | 8/1972 | McCormick | 128/214 R |
| 3,924,636 | 12/1975 | Addison | 128/351 |
| 4,221,215 | 9/1980 | Mandelbaum | 128/155 |
| 4,313,437 | 2/1982 | Martin . | |
| 4,315,505 | 2/1982 | Crandall et al. | 128/200.26 |
| 4,326,515 | 4/1982 | Shaffer et al. . | |
| 4,331,144 | 5/1982 | Wapner | 128/207.17 |
| 4,548,200 | 10/1985 | Wapner | 128/207.17 |
| 4,658,813 | 4/1987 | Jones . | |
| 4,817,598 | 4/1989 | LaBombard . | |
| 4,915,694 | 4/1990 | Yamamoto et al. | 604/180 |
| 5,009,227 | 4/1991 | Nieuwstad . | |
| 5,060,645 | 10/1991 | Russell . | |
| 5,146,913 | 9/1992 | Khorsandian et al. . | |
| 5,344,411 | 9/1994 | Domb et al. | 604/265 |
| 5,471,980 | 12/1995 | Varner | 128/207.17 |
| 5,512,055 | 4/1996 | Domb et al. | 604/265 |
| 5,529,062 | 6/1996 | Byrd | 128/207.17 |
| 5,555,881 | 9/1996 | Rogers et al. | 128/207.17 |
| 5,653,232 | 8/1997 | Rogers | 128/207.17 |
| 5,671,732 | 9/1997 | Bowen | 128/207.17 |
| 5,762,638 | 6/1998 | Shikani et al. | 604/265 |
| 5,778,877 | 7/1998 | Stuart | 128/207.17 |
| 5,782,236 | 7/1998 | Ess | 128/207.17 |
| 5,819,734 | 10/1998 | Deily et al. | 128/207.17 |
| 5,918,599 | 7/1999 | Shesol | 128/207.17 |

*Primary Examiner*—Aaron J. Lewis
*Assistant Examiner*—Teena Mitchell
*Attorney, Agent, or Firm*—Kennedy Covington Lobdell & Hickman, LLP

[57] ABSTRACT

A device for supporting and retaining a tracheostomy tube or an endotracheal tube of the type having a tube including a flexible support flange and an inner cannula having a locking means which connects the inner cannula to the tube. The device includes a holder base having a uniquely shaped tube receiving opening designed to securely retain the tube therein and which includes at least one through-slot extending outward from the opening for receiving the locking means therethrough and preventing contact between the locking means of the inner cannula and the holder base. The device includes a removable tab which extends into the opening, a removable support strap for releasably securing the holder to the patient and an anchor strap for anchoring a circuit in place. In alternate preferred embodiments, the tube receiving opening may be triangular or any number of shapes and include through slots extending outward therefrom, and the body is a narrow portion which allows the face of the support flange to remain visible when the holder base is positioned for use.

16 Claims, 8 Drawing Sheets

ADVANCED TRACHEOSTOMY TUBE AND ORAL ENDOTRACHEAL TUBE HOLDER

BACKGROUND OF THE INVENTION

The present invention relates to devices for securing tracheostomy tubes and oral endotracheal tubes and more particularly, relates to an improved tracheostomy tube and oral endotracheal tube holder for retaining such tubes in operational, patient contact.

A tracheostomy tube is a curved tube which is inserted into a tracheostomy stoma. While there are several different types of tubes, they all have similar parts. The main parts of a tracheostomy tube are the outer tube, the inner tube or inner cannula and the obturator. The obturator is only used to insert the outer tube and is removed once the outer tube is in place. The outer tube typically has a support base flange and ties to secure around the patient's neck. In use, the inner cannula is inserted and removably locked in place after the obturator is removed. The inner cannula is withdrawn for brief periods to be cleaned and acts as a removable liner for the more permanent outer tube. Tracheostomy tubes may be cuffed, uncuffed or fenestrated. A cuff is a soft balloon around the tracheostomy tube near the distal end that can be inflated to hold the tube in place.

Prior to 1983, the only method being used to any extent to secure a tracheostomy tube to a patient's neck was strips of cotton fabric split at either end and then tied through the openings in the flange of the trache. Although reliable, it was extremely time consuming and tended to fray at the ends and roll up in a rope configuration which caused irritation to the patient's neck. Wapner U.S. Pat. No. 4,331,144 addressed these problems. Wapner U.S. Pat. No. 4,331,144 discloses a band which encircles the head and secures to itself using a hook and loop fastener. It also employs strips which thread through the slits in a trache flange and then secures back onto itself using hook and loop fasteners. While certainly functional, the Wapner device is also time consuming and can be extremely difficult to employ if the flange of the trache holder is pulled into folds of flesh as is often the case with overweight patients. To overcome this problem, the inward force normally required to hold trache tube within the trachea must be reduced in order to allow the flanges to ride above the flesh folds. This scenario can result in the trache tube actually coming out of the stoma in the trachea. Examples of other tracheostomy tube holders are shown in U.S. Pat. No. 5,529,062 issued to T. N. Byrd on Jun. 25, 1996 and U.S. Pat. No. 5,671,732 issued to M. L. Brown on Sep. 30, 1997.

With regard to securing oral endotracheal tubes, the generally practiced method is to use tape which is wrapped around a patient's neck and is then wrapped around the tube itself before being adhered to a patient's cheek for anchoring purposes. This technique is also time consuming and the tape needs to be replaced frequently due to saliva and blood which decreases the adhesive ability of the tape. Addison U.S. Pat. No. 3,924,636 and Wapner U.S. Pat. No. 4,548,200 illustrate attempts to standardize and simplify the securing of oral endotracheal tubes. Wapner U.S. Pat. No. 4,548,200 discloses a device which employs a hook and loop fastener with adhesive backing which encircles the patient's head. Since it employs a soft material in the region of the mouth, the tube holder would become stained and slippery in short order and would necessitate frequent replacement. Further, the device of Wapner '200 is not applicable to a tracheostomy tube. Addison U.S. Pat. No. 3,924,636 discloses a plastery with a central opening and a holding strap that is self-adhering. The Addison device, since it can stick to the patient's face by means of an adhesive plastery, cannot be used if the patient has any type of facial injury since it cannot be taped over a wound site, and the elliptical central opening does not prevent any lateral tube migration. It is also not applicable to a tracheostomy tube.

The present invention is specifically directed to an improvement in the type of holder shown in my U.S. Pat. No. 5,471,980 entitled "Tracheostomy Tube and Oral Endotracheal Tube Holder" issued on Dec. 5, 1995. This patent discloses a device for supporting and retaining a tracheostomy tube or endotracheal tube in operational patient contact and includes a support strap, a tube support member having an opening formed therein and at least one resilient tube engagement member projecting into the tube receiving opening for contacting and frictionally retaining a tube in the opening. As is typical, the tracheostomy tube for which this holder is designed includes a support flange with openings for receiving ties and a barrel, at one end of the tube adjacent to the support flange, including a lip extending along the opening of the tube. The tube holder comprises a generally flat, elongate main body portion including a tube receiving opening at its midpoint and first and second straps attached to its ends. The tube receiving opening includes has a plurality of resilient tube engagement members. The main body of the tracheostomy tube holder is approximately the same size and configuration as the support flange of the tracheostomy tube.

In use, the main body is positioned against the support flange so that the barrel of the tracheostomy tube is received through the tube receiving opening and secured therein by the tube engagement members. Thus, the holder is positioned over and covers the support flange and is securely mounted to the tracheostomy tube. Unlike prior art methods for securing the tracheostomy tube to the patient which require attaching ties directly to the support flange, the support strap of my patented device is connected to the holder which securely holds the holder and tracheostomy tube in place on the patient. The patient is connected to a ventilator via a circuit which is connected to an inner cannula tube including locking means which extend into the underside of the lip and lock onto the lip of the barrel of the tracheostomy tube to connect the inner cannula and the tracheostomy tube. In order to attach the tube to the flange while allowing the tube to move relative to the flange, the tracheostomy tube typically includes articulations or pivots on the exterior of the tube adjacent to the barrel, which extend outward onto the surface of the support flange forming raised portions on the flange adjacent to the barrel. The articulations increase the flexibility of the flange relative to the tube. Thus, the tube may move relative to the flange in response to movement of the patient's head and neck and provide for better comfort of the patient without the possibility of disconnection between the support flange and the tracheostomy tube.

While the tracheostomy tube holder shown in U.S. Pat. No. 5,471,980 provides a simple and effective means for holding a tracheostomy or endotracheal tube in operational patient contact, one disadvantage is that the articulations or pivots of the tube and flange do not permit the main body of the tube support member and the support flange to be positioned completely flush with one another. Because prior art methods typically utilize the openings on the support flange to secure the tracheostomy tube to the patient, the locking means of the cannula is designed to lock onto the lip of the barrel of the tracheostomy tube with little clearance between the locking means and the support flange.

Therefore, because the main body and flange are not flush, the addition of the main body of the holder between the support flange and the teeth of the inner cannula in the area where the teeth lock onto the underside of the lip of the barrel may impair the grip of the teeth on the tracheostomy tube and prevent a secure connection between the inner cannula, and the tube and the patient and the ventilator.

Figure 1:
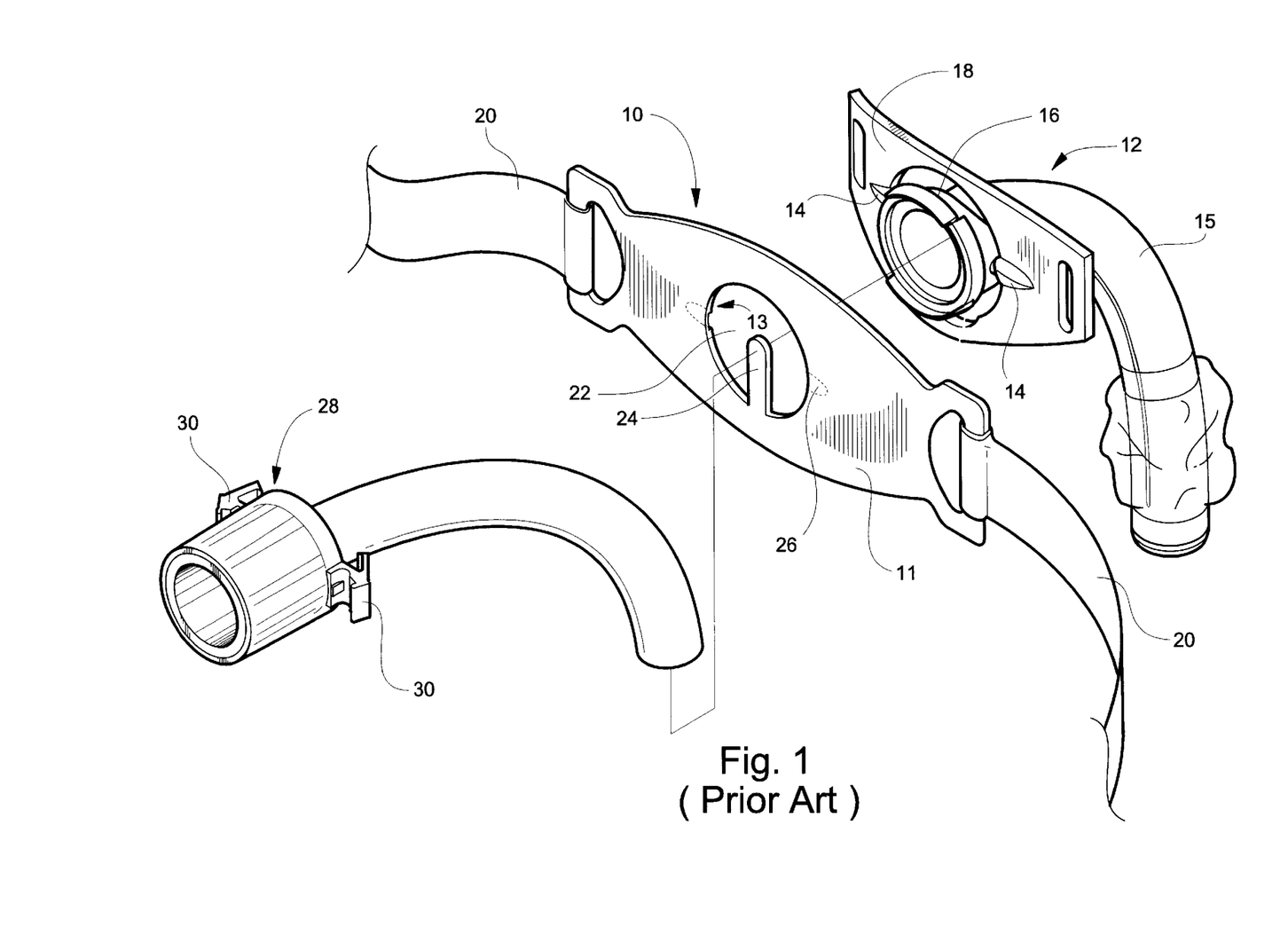
FIG. 1 (PRIOR ART) is an exploded view of the prior device for supporting and retaining a tracheostomy or endotracheal tube in operational patient contact and showing an inner cannula to be connected to a tracheostomy tube having articulations or pivots on the support flange.
Figure 2:
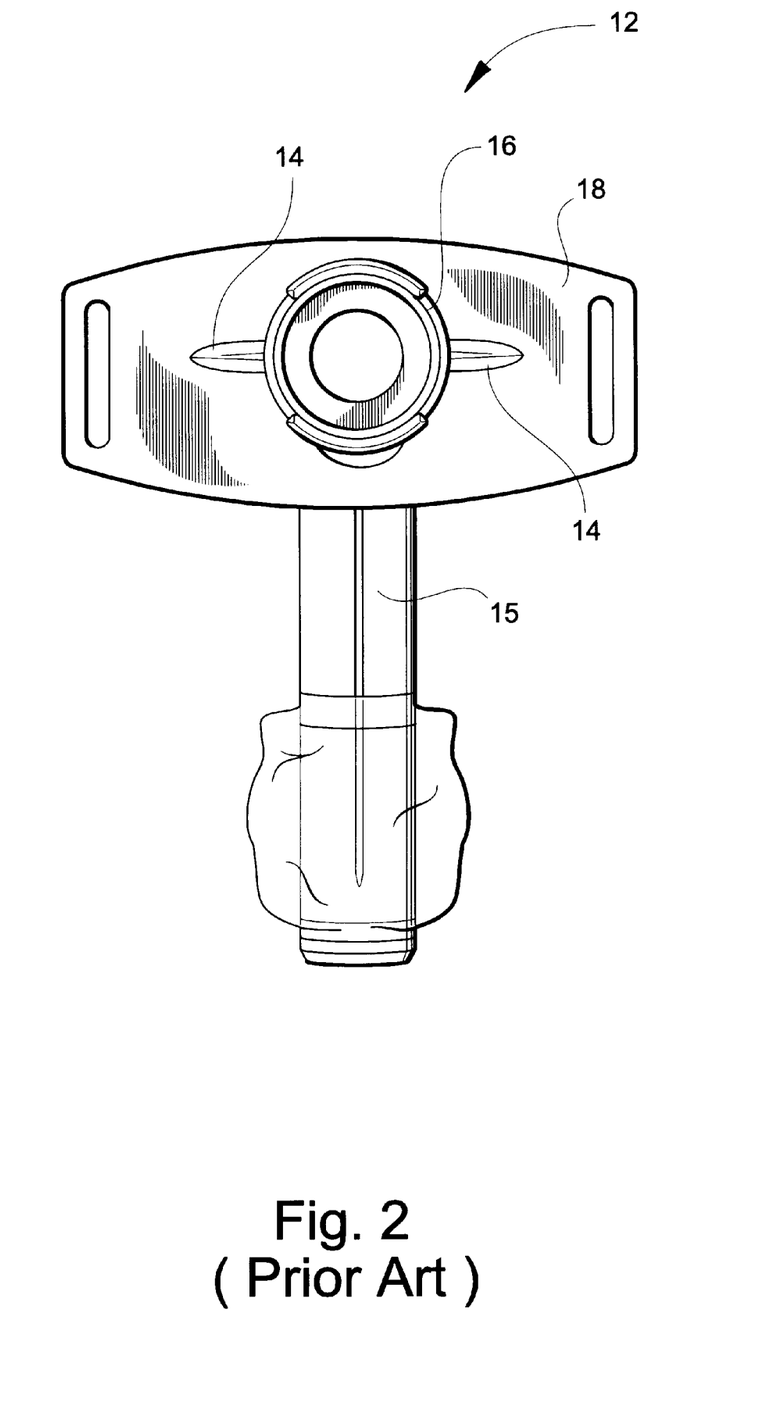
FIG. 2 (PRIOR ART) is a front view of the support flange of the tracheostomy tube.
Figure 3:
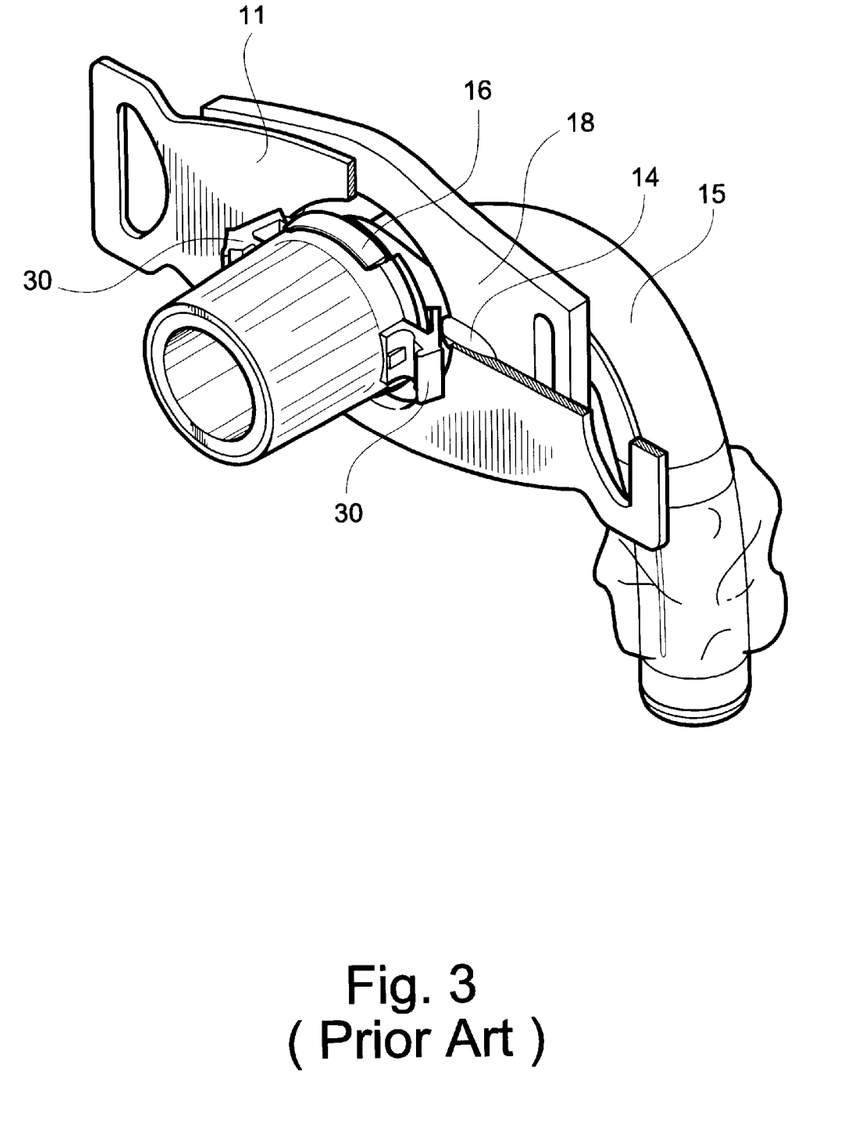
FIG. 3 (PRIOR ART) is a perspective and partial cross-sectional view showing the support base flange flush with the tube holder base and the gripping portion of an inner cannula connected to the device.

One method of addressing this serious problem is shown in my improved tracheostomy holder at FIGS. 1–3 (PRIOR ART) of this application. The improved tracheostomy holder includes a main body portion having a tube receiving opening at its midpoint and straps attached to its ends. The tube receiving opening includes a resilient tube engagement member which may be removed or used to secure an oral endotracheal tube or further secure a tracheostomy tube in place. The improved tracheostomy holder also includes an additional strap for anchoring the strap in place and means for securing the anchor strap around the circuit after the inner cannula is locked in place and the circuit connecting the ventilator thereto is attached to the inner cannula. In addition, the main body may also be formed of an anti-microbial material, such as, by way of example, a plastic impregnated with a broad spectrum anti-microbial agent, for reducing bacteria at the tracheostomy opening and reducing the risk of infection.

In order to permit a secure connection between the inner cannula and the tracheostomy tube, the main body of the improved tracheostomy holder has a back surface including shallow, triangular-shaped recesses or indentations which allow the main body to rest completely flush with the support flange of the tracheostomy tube. In use, the support flange is positioned flush with the main body so that the barrel of the tracheostomy tube is received through the tube receiving opening and secured therein by the tube engagement member and the device is secured to the patient with the straps attached thereto. When the tube is in place for connection to the inner cannula, the articulation or pivots of the tube and support flange mate with and project into the shallow, triangular-shaped recesses on the back surface of the main body so that the main body and support flange of the tracheostomy tube are completely flush with one another. Because the main body and support flange are completely flush, the grip of the teeth of the inner cannula on the tube is not impaired for providing a secure connection between the patient and the ventilator.

In an ongoing effort to increase patient comfort, there has recently been an improvement to tracheostomy tubes. The improvement provides tracheostromy tubes with a support flange constructed of a softer, more flexible yet durable material such as, by way of example, rubberized plastic. Because the support flange rests directly against the patient's throat, the use of a softer, more flexible material may substantially reduce the irritation which may be caused by the contact of the support flange with the patient's skin. While the improved support flange remains substantially the same shape, the use of the softer, more flexible material has increased the thickness of the support flange. Therefore, the articulations or pivots heretofore known to be on the exterior of the tube and flange are now encompassed within the interior of the thicker support flange and there are no raised portions on the exterior of the flange adjacent to the barrel of the tube.

While my improved tracheostomy holder may be ideal for use with tracheostomy tubes which include articulations or pivots on the exterior of the tube adjacent to the barrel forming raised portions on the support flange adjacent to the barrel, this device has not proven effective with the recently improved tracheostomy tubes which include the thicker, flexible, soft support flange. Although the main body is flush with the support flange, the improved, thicker, flexible support flange effectively decreases the clearance from the front of the flange to the underside of the lip of the barrel leaving no space for the addition of the main body between the flange and the teeth of the cannula for allowing the teeth to lock onto the lip of the tracheostomy tube. Further, the shallow, triangular-shaped indentations on the back surface of the main body do not address the problem since the articulations of the improved flange are formed within the interior of the flange and no longer extend into or mate with the indentations of the device. Thus, the grip of the cannula teeth on the improved tracheostomy tube with a flexible support flange is impaired or completely prevented by this type of tracheostomy tube holder including indentations in the back surface of the main body. Therefore, there is a need for an improved tracheostomy or endotracheal tube holder which provides a means for allowing the teeth of the inner cannula to securely grip a tracheostomy tube without impairment, regardless of the thickness of the support flange, while maintaining the flexibility of the flange and comfort of the patient and providing a simple and effective means for holding a tracheostomy or endotracheal tube.

SUMMARY OF THE INVENTION

The present invention is directed to an improved tracheostomy and endotracheal tube holder for tracheostomy and endotracheal tubes of the type having an outer tube including a soft, flexible support flange, a barrel at one end of the tube adjacent to the support flange and an inner cannula having locking means which lock onto a lip of the barrel for securely connecting the inner cannula and the tube. The improved tracheostomy holder of the present invention includes a uniquely shaped holder base specifically designed for tightly securing an improved soft tracheostomy or endotracheal tube to a patient while allowing the teeth of the inner cannula to securely grip the lip of the barrel of the tube without impairment.

The present invention is specifically directed to an improved tracheostomy and endotracheal tube holder which includes a holder base having a uniquely shaped tube receiving opening designed to prevent lateral movement of the tube for securely retaining the tube therein and including at least one through-slot extending outward from the opening for preventing contact between the locking means of the inner cannula and the holder base. The preferred holder base has a body which is substantially the same size and configuration of the support flange and in use, is positioned directly over the support flange. In the preferred embodiment, a removable, resilient tab extends into the opening and a pair of slots extend outward from the perimeter of the tube receiving opening and are positioned to correspond to the locking means, such as, by way of example, the standardized gripping teeth of a typical inner cannula. Each through-slot defines a substantially rectangular-shaped through hole which is dimensioned to allow close passage of the teeth therethrough.

In use for retaining a tracheostomy tube, the resilient tab is preferably removed and the holder base is positioned over the support flange with the barrel of the tracheostomy tube projecting through the opening and fitting snugly within the opening. Alternatively, while retaining an oral endotracheal tube, the resilient tab of the holder is not removed and engages and is taped to the tube extending through the tube receiving opening for preventing the vertical movement of the tube within the opening. This provides a substantial improvement over the current method of applying tape to the patient's face to limit movement of the oral endotracheal tube. While the resilient tab is typically removed when the holder is utilized to retain a tracheostomy tube, the tab may be left in place, as desired, for engaging and further securing the tube in the opening.

In the preferred embodiment, the tube receiving opening is substantially pear-shaped having a larger diameter portion and a smaller diameter portion. The uniquely shaped opening permits either large or small diameter tubes to pass through the opening while providing a snug fit around the tube to prevent lateral movement of the tube by allowing the barrel of the tube to be received through the larger portion of the opening and then positioning the tube in the smaller portion therein. Because the slots extending outward from the opening eliminate any obstruction from the front side of the support flange and the underside of the lip of the barrel, the teeth of the inner cannula may securely grip the lip of the barrel without impairment and provide a secure connection between the inner cannula and the tracheostomy tube. In addition, the slots facilitate the assembly of the holder base on the support flange by providing additional clearance for the lip of the barrel as the barrel is received through the tube receiving opening and the holder base is positioned for use. Thus, the unique design of the present invention provides a simple and effective tube holder for securely supporting and retaining a tracheostomy or endotracheal tube comfortably on a patient while eliminating the possibility that the tube holder will interfere with the secure connection of the inner cannula and the tracheostomy tube.

In addition, the preferred embodiment of the present invention includes a removable support strap for releasably securing the holder to the patient and an anchor strap for anchoring the circuit in place. While the tracheostomy tube itself is usually changed every one or two weeks to prevent mucus build up and for cleanliness, the tracheostomy tube holder may be changed numerous times, such as when the patient bathes, saliva or vomit is deposited on the strap or if the patient cuts themselves, and is typically changed everyday. Because the patient's immune system is compromised with the insertion of the tracheostomy tube, the patient is particularly susceptible to infection. Thus, in the preferred embodiment, the holder base is formed of an anti-microbial plastic, such as, by way of example, a plastic impregnated with a broad spectrum anti-microbial agent, and the support strap is immersed in or otherwise includes an anti-microbial agent, such as, by way of example, a broad spectrum anti-microbial agent, for decreasing the risk of infection.

In an alternative preferred embodiment, the tube receiving opening is substantially triangular-shaped having a large triangle base portion at the top of the opening and side walls which extend downward to a point at the bottom of the opening and includes at least one through-slot extending outward from the opening for receiving the locking means of an inner cannula therethrough. The uniquely shaped triangular opening permits various different sized tracheostomy or oral endotracheal tubes, even oversized or extremely small tubes, to be easily inserted into the opening while the triangle walls form a snug fit with the tube once it is positioned to prevent lateral migration of any sized tube. While pear-shaped and triangular-shaped openings are discussed herein, any number of shapes, including but not limited to, circular, eliptical, or trapezoidal shaped openings which include slots extending outward from the opening for passing therethrough the teeth of the inner cannula, may be suitable for the tube receiving opening of the present invention. In another preferred embodiment, the body of the holder base is not shaped or sized similarly to the support flange but forms a narrow portion extending a short distance outward from and around the entire perimeter of the tube receiving opening and includes means for securing the support strap to each end of the holder base. In this embodiment, the face of the support flange of the tracheostomy tube remains advantageously visible while the tube holder supports and retains the tracheostomy tube to the patient. Thus, the tracheostomy tube information, such as by way of example "6 DCT I.D.7.0 O.D.10.0", which is typically printed on the face of the support flange can easily be viewed by doctors, nurses or caretakers without removing the tube holder. In addition, the face of the support flange can readily be cleaned without removing the tube holder.

Therefore, it is an object and feature of the present invention to provide an improved tracheostomy tube and oral endotracheal tube holder which includes a uniquely shaped holder base specifically designed for securing an improved soft tracheostomy or endotracheal tube to a patient while allowing the locking means of the inner cannula to securely grip the lip of the barrel of the tube without impairment.

It is a further object and feature of the present invention to provide an improved tracheostomy tube and oral endotracheal tube holder having a uniquely shaped tube receiving opening which prevents lateral movement of the tube for securely retaining the tube therein and including at least one through-slot extending outward from the opening for preventing contact between the locking means of the inner cannula and the holder base.

It is another object and feature of the present invention to provide a holder base having a tube receiving opening which includes substantially rectangular-shaped through-slots which are positioned to correspond to the standardized gripping teeth of a typical inner cannula and is dimensioned to allow close passage of the teeth therethrough when the teeth are locked in place.

It is yet another object and feature of the present invention to provide an improved tracheostomy tube and oral endotracheal tube holder which includes a removable strap immersed in broad spectrum anti-microbial agent for releasably securing the holder to the patient and decreasing the risk of infection.

Further details, features and advantages of the invention can be understood from the exemplary embodiments described in the following description with reference to the accompanying drawings.

DETAILED DESCRIPTION OF THE PREFERRED EMBODIMENT

FIGS. 1, 2 and 3 illustrate the prior art tracheostomy tube holder 10 which is an improvement of the tracheostomy tube holder disclosed in my U.S. Pat. No. 5,471,980. As best seen in FIGS. 1 and 2, the prior art tracheostomy tube 12 includes pivots or articulations 14 on the exterior of an outer tube 15, adjacent to the tube barrel 16, which extend outward onto the surface of the tube support flange 18 forming raised portions on the flange 18 adjacent to the barrel 16. As shown in FIG. 1, the main body 11 of the prior art tracheostomy tube holder 10 has straps 20 attached to its ends and includes a tube receiving opening 22 which has a resilient tab 24 extending into the opening 22. The back surface 13 of the main body 11 includes shallow triangularshaped recesses or indentations 26 adapted to receive the articulations of the support flange 18. The inner cannula 28 which includes locking teeth 30 for gripping the lip of the barrel 16 and securing the inner cannula 28 to the tracheostomy tube 12 is also shown in FIG. 1.

In use, the main body 11 of the prior art tube holder 10 is placed over the support flange 18 with the barrel 16 of the tracheostomy tube 12 extending through the opening 22 and the articulations 14 mating with and projecting into the shallow triangular indentations 26 so that the main body 11 and support flange 18 of the assembled device are completely flush with one another. As shown in FIG. 3, the position of the prior art tube holder 10 flush against the support flange 18 provides enough clearance between the main body 11 and the underside of the lip of the barrel 16 to allow the teeth of the cannula to grip the barrel of the tube 12. While the prior art tube holder is designed to accommodate the articulations of the tracheostomy tube to permit a secure connection between the inner cannula and the tube, the prior art tube holder has not proven effective with the new, improved tracheostomy tubes. The new tubes are constructed of a softer, more flexible material which encompasses the articulations 14 which previously extended outward from the tube support flange 8. With the articulations 14 eliminated, the shallow recesses 26 on the back surface 13 of the prior art tube holder 10 to accommodate the articulations are no longer necessary. While the assembled tube holder and the new support flange are flush with one another, one problem of the thicker, flexible support flange is that it decreases the clearance from the front of the flange to the underside of the lip of the barrel leaving no space for the addition of the main body between the flange and the barrel. Thus, when the tube holder is in place, there is not enough space to allow the teeth of the inner cannula to lock onto the lip of the tracheostomy tube.

The tracheostomy tube holder 110 of the present invention addresses the problem caused by the improved tracheostomy tube having a thicker support flange and provides a tracheostomy tube holder with a uniquely shaped holder base which allows the teeth of an inner cannula to securely grip the barrel of the tracheostomy tube without impairment.

Figure 4:
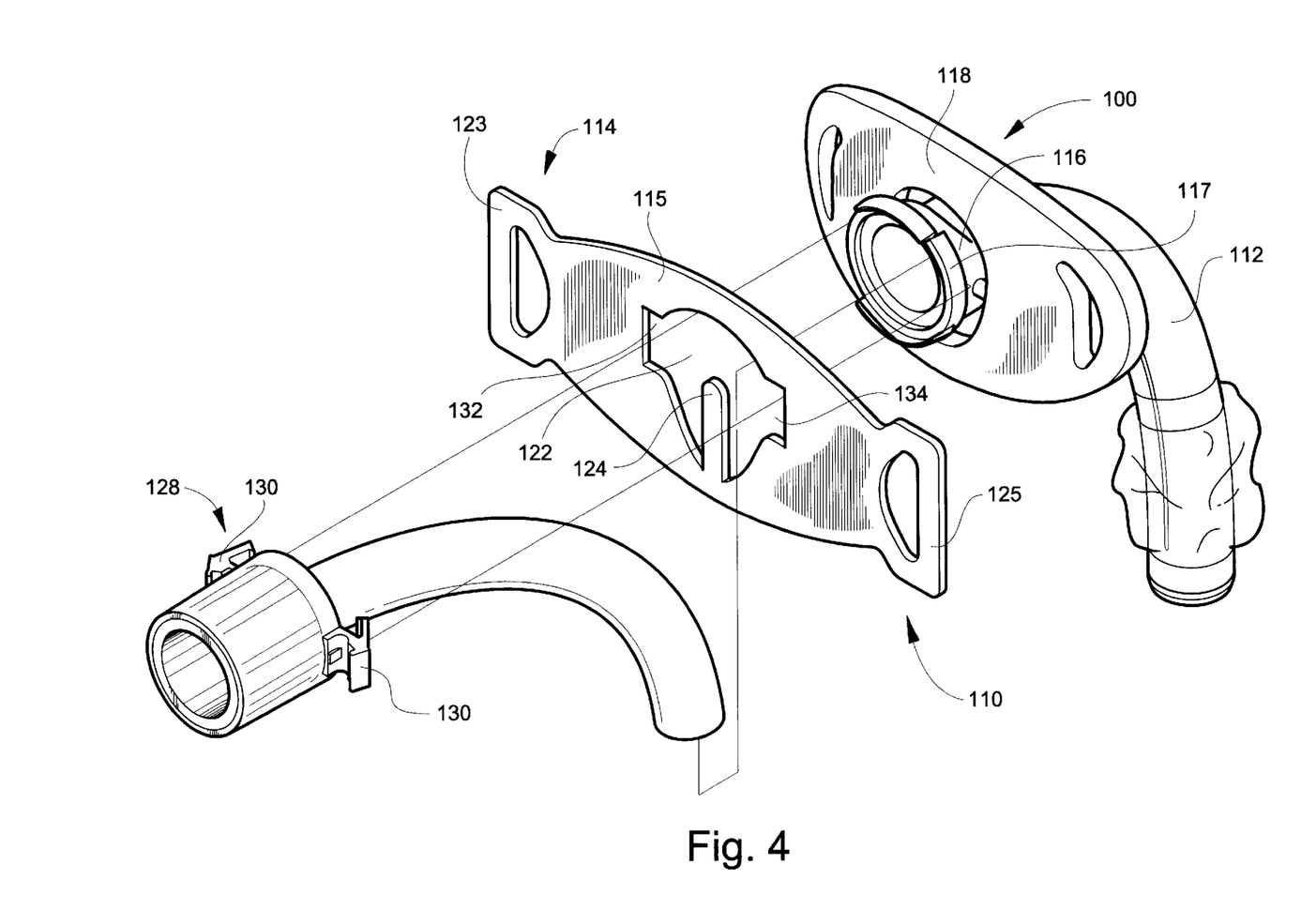
FIG. 4 is an exploded view of the improved tracheostomy tube and endotracheal tube holder illustrating the holder base and uniquely shaped tube receiving opening and showing an inner cannula to be connected to a lip of the barrel of a tracheostomy tube having a flexible support flange.

The present invention is shown in FIGS. 4–9 and is directed to an improved tracheostomy and endotracheal tube holder 110 for tracheostomy and endotracheal tubes 100 of the type having an outer tube 112 including a soft, flexible support flange 118, a barrel 116 at one end of the tube 112 adjacent to the support flange 118 and an inner cannula 128 having locking means which lock onto a lip 117 of the barrel 116 for securely connecting the inner cannula 128 and the tube 112. The present invention is specifically directed to a holder base 114 which includes a body 115 having a uniquely shaped tube receiving opening 122 designed to prevent lateral movement of the tube 112 extending therethrough. In the preferred embodiment, the tube receiving opening 122 is substantially pear-shaped having a large diameter portion at the top and a smaller diameter portion at the bottom of the pear-shaped opening 122. As best seen in FIG. 4, the preferred holder base 114 includes opposite ends 123, 125 and a pair of through slots 132, 134 extending outward from opposite sides of the opening 122. The body 115 of the holder base 114 is substantially the same size and configuration of the support flange 118 and in use, is positioned directly over the support flange 118. In the preferred embodiment, a removeable resilient tab 124 extends into the opening 122 and is preferably perforated for easy removal when the holder base 114 is placed in position over the support flange 118 with the barrel 116 of the tube 112 projecting through the opening 122.

Figure 5:
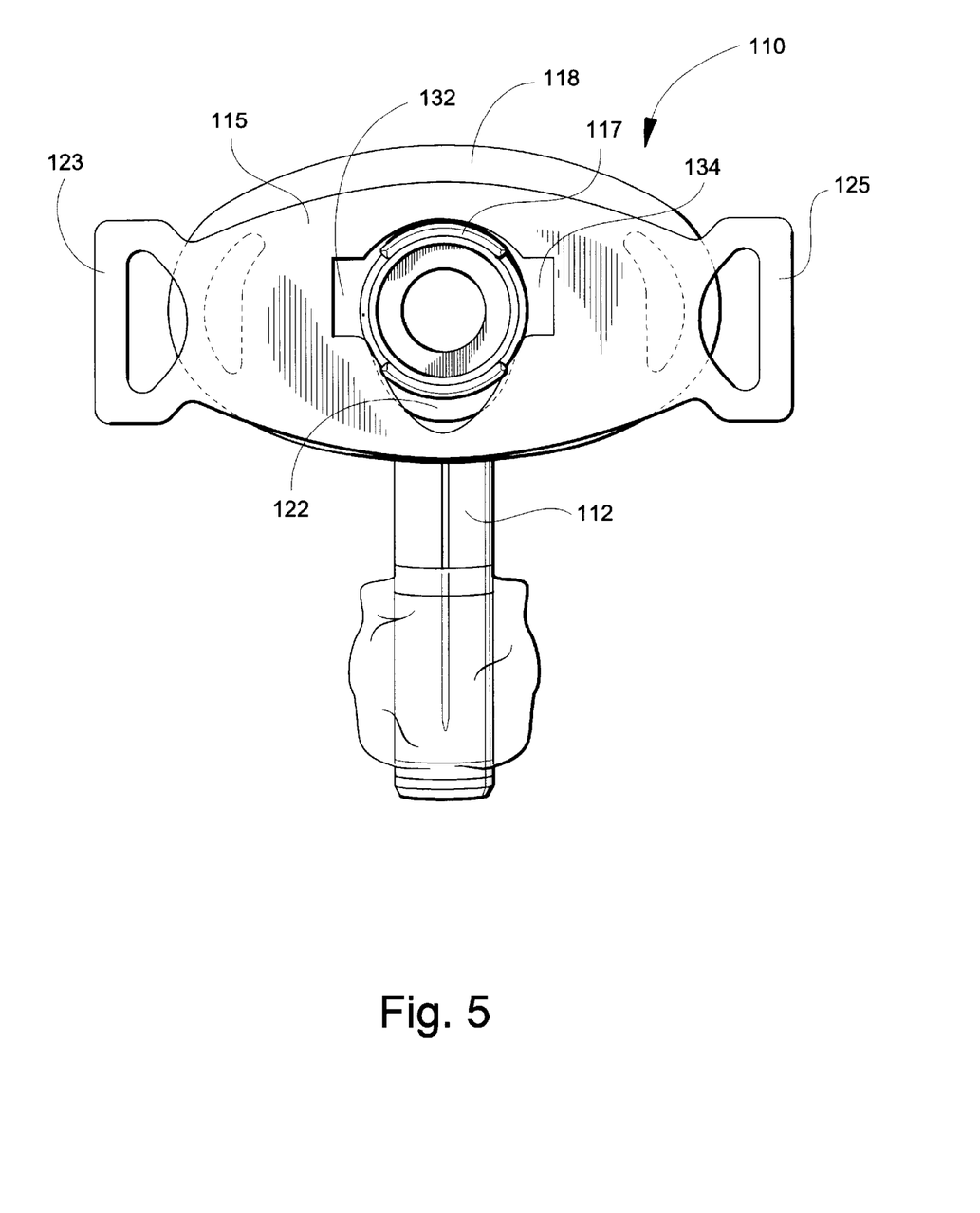
FIG. 5 is front perspective view of the assembled device showing the holder base positioned on the support flange which is shown in phantom prior to connecting the inner cannula.
Figure 6:
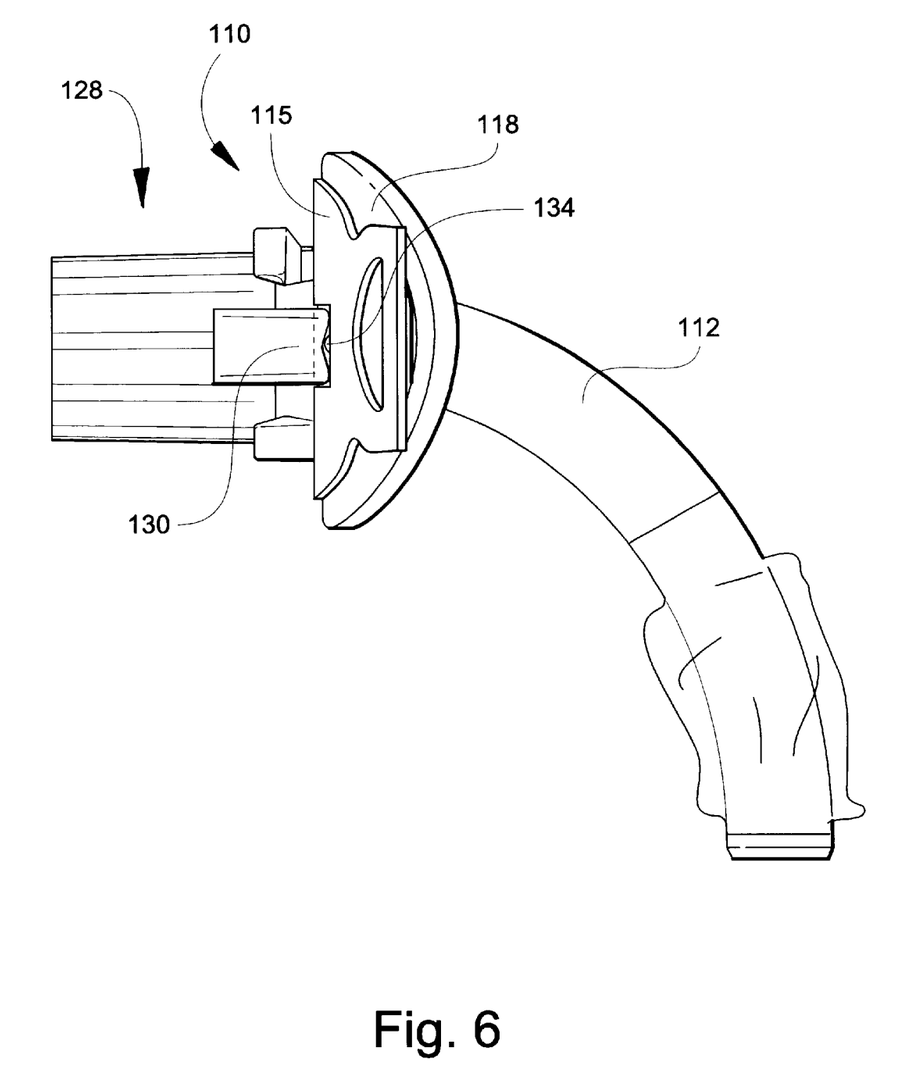
FIG. 6 is a side view of the assembled device showing the teeth of the inner cannula locked onto the barrel of the tracheostomy tube.

As shown in FIGS. 4 and 6, the locking means of the inner cannula 128 are a pair of locking or gripping teeth 130 and the slots 132, 134 are positioned to correspond to the gripping teeth 130. As shown in FIGS. 4 and 5, each through slot 132, 134 defines a substantially rectangular shaped through hole which allows the teeth 130 to securely grip the lip 117 of the barrel 116 without contacting the holder base 114. As best seen in FIG. 6, each through slot 132, 134 is dimensioned to allows close passage of the teeth 130 therethrough to securely grip the lip 117 of the barrel 116 without impairment and provide a secure connection.

Figure 7:
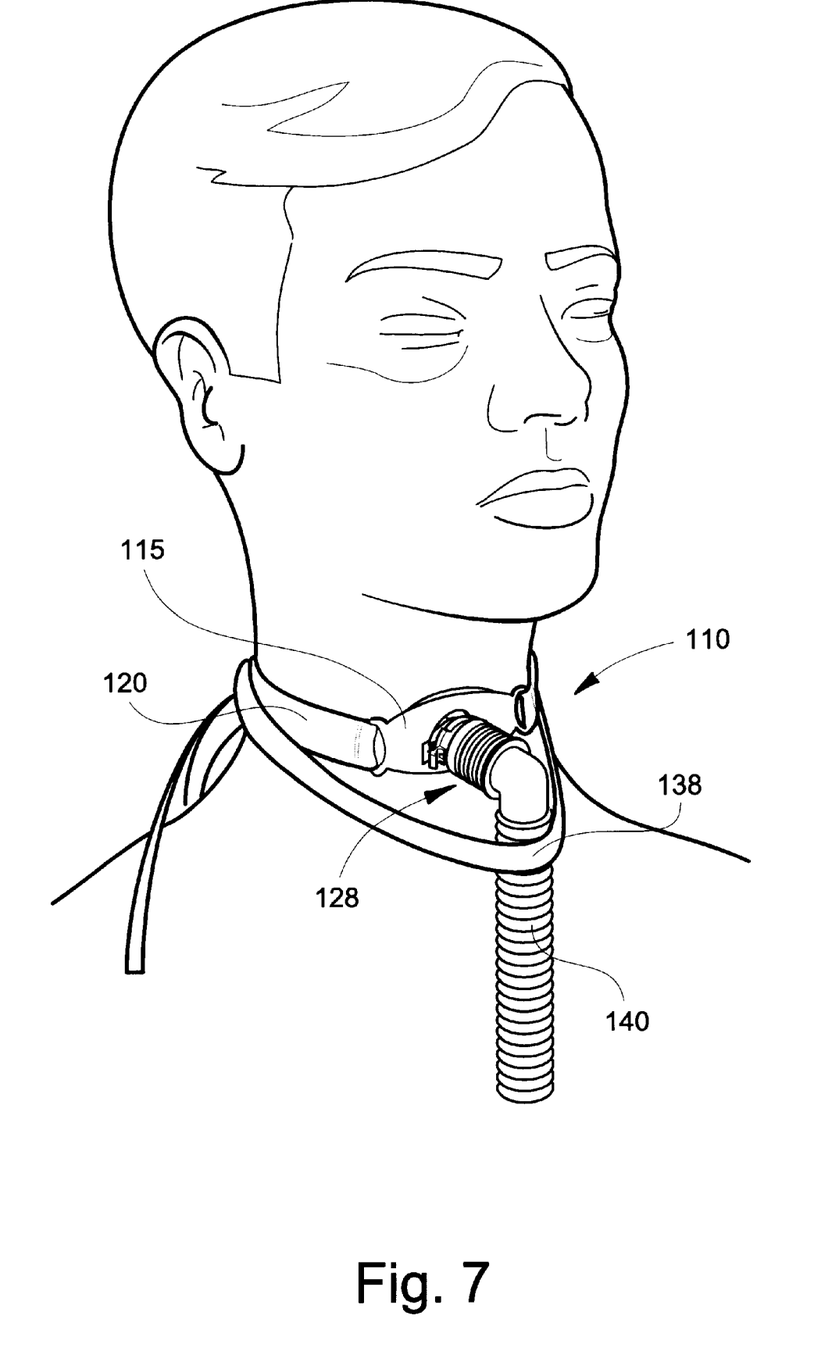
FIG. 7 is a perspective view of the improved tracheostomy tube and endotracheal tube holder illustrating the device in use securing and retaining a tracheostomy tube to a patient and including an anchor strap over the circuit.

In use, the holder base 114 is placed over the support flange 118 with the barrel 116 of the tube 112 extending through the opening 122 and the holder base 114 is secured to the patient. As shown in FIG. 7, the preferred embodiment of the present invention includes a removeable support strap 120 attached to the ends 123, 125 of the body 115 for reseasably securing the holder 110 to the patient. The inner cannula 128 is connected to the tube 112 with the teeth 130 of the inner cannula 128 extending through the slots 132, 134 to securely grip the lip 117 of the barrel 116 (see FIGS. 6 and 7). The preferred embodiment also includes an anchor strap 138, as shown in FIG. 7, for securing a circuit 140 in place. The preferred holder base 114 is formed of an anti-microbial plastic and the preferred support strap 120 is immersed or otherwise includes an anti-microbial agent for decreasing the risk of infection.

Figure 8:
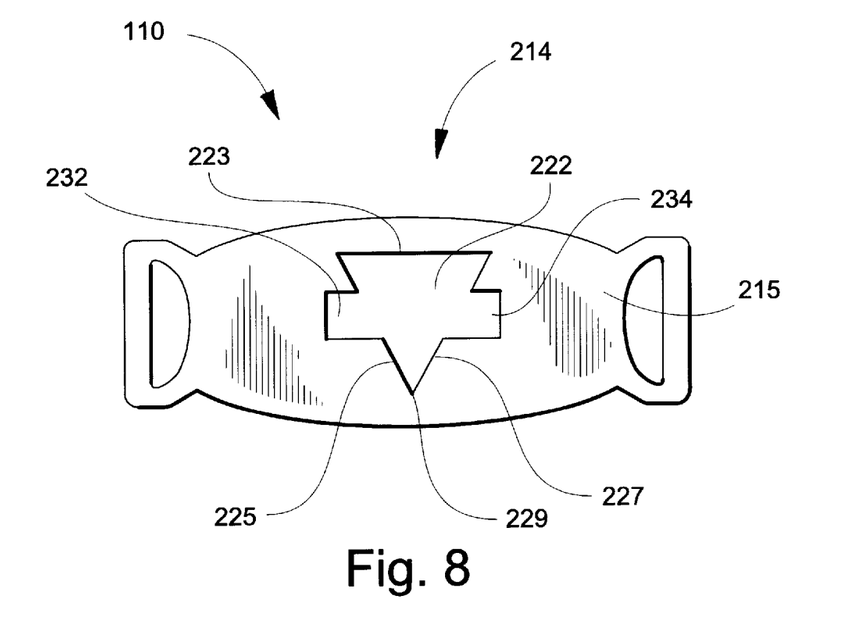
FIG. 8 is a front view of an alternative preferred embodiment of the holder base having a triangular-shaped tube receiving opening.
Figure 9:
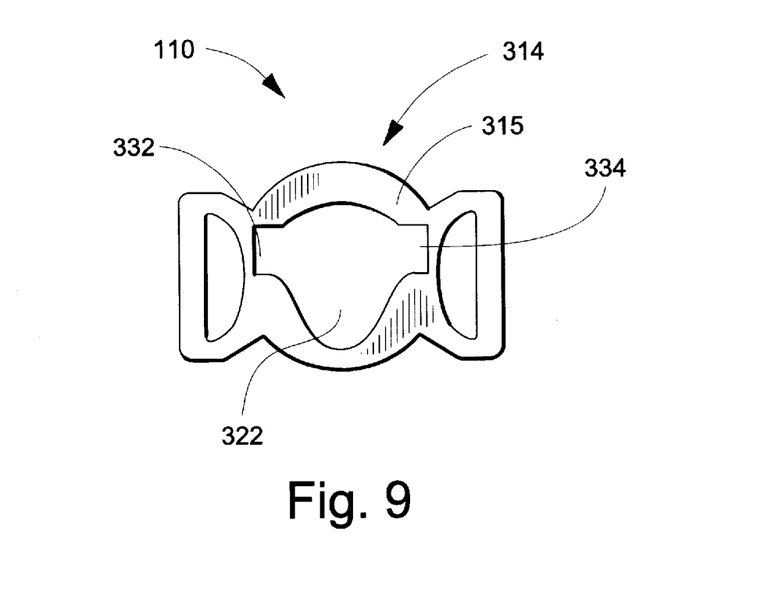
FIG. 9 is a front view perspective view of another preferred embodiment of the device including a holder base which does not extend over the face of the support flange.

FIGS. 8 and 9 illustrate alternate preferred embodiments of the present invention. In one alternate preferred embodiment shown in FIG. 8, a holder base 214 includes a body 215 having a tube receiving opening 222 which is substantially triangular shaped with a large triangle base portion 223 at the top of the opening and side walls 225, 227 which extend downward to a point 229 at the bottom of the opening. This uniquely shaped triangle opening 222 permits various different sized tracheostomy or oral endotracheal tubes, even oversized or extremely small tubes, to be easily inserted into the opening 222 while the triangle walls 225, 227 form a snug fit with the tube once it is positioned to prevent lateral migration of any sized tube. As shown in FIG. 8, the uniquely shaped opening 222 includes through slots 232, 234 for preventing contact between the locking teeth of an inner cannula and the holder base 214 when the inner cannula is connected to the tube. FIG. 9 illustrates another preferred embodiment of the present invention which includes a holder base 314 having a narrow body or portion 315 extending a short distance outward from and around the entire perimeter of a tube receiving opening 322 which includes through slots 332, 334. Because the holder base 314 of this preferred embodiment is not shaped or sized similarly to the support flange of the tube, the face of the support flange remains visible when the holder base 314 is positioned over the support flange for use.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A tube holder for supporting and retaining a tracheostomy tube or an endotracheal tube of the type having a tube and tube support flange, an inner cannula for insertion into the tube and inner cannula locking means for securing the inner cannula to the tube, the tube holder comprising a holder base having a body including a tube receiving opening adapted for receiving a barrel of a tube therethrough and further including a through-slot extending laterally outward from and adjacent to the opening, the through-slot being adapted for extension therethrough of an inner cannula locking means for securement to a tube without interference between the inner cannula locking means and the holder base.

2. The tube holder of claim 1, wherein the tube receiving opening is adapted to prevent lateral movement of a tube received therethrough for tightly securing a tube in the opening.

3. The tube holder of claim 2, wherein the tube receiving opening includes a first portion and a second portion, the first portion having a diameter larger than the diameter of the second portion.

4. The tube holder of claim 3, wherein said tube receiving opening is substantially pear-shaped.

5. The tube holder of claim 3, wherein the tube receiving opening is substantially triangular-shaped.

6. The tube holder of claim 1, wherein the tube receiving opening includes a pair of slots extending outward from and adjacent to the opening and being positioned to correspond to a locking means of an inner cannula when an inner cannula is locked onto a tube.

7. The tube holder of claim 1, wherein each slot is dimensioned for allowing close passage of a locking means of an inner cannula through the slots.

8. The tube holder of claim 1, wherein the body of the holder base is substantially the same size and shape as a support flange of a tube.

9. The tube holder of claim 1, wherein the body of the holder base defines a narrow portion extending along the perimeter of the tube receiving opening.

10. The tube holder of claim 1, wherein the holder base includes a support strap attached to the holder base for releasably securing the tube holder to a patient.

11. The tube holder of claim 10, wherein the support strap is immersed in an anti-microbial agent for reducing the risk of infection.

12. The tube holder of claim 11, wherein the holder base is formed of an anti-microbial material.

13. The tube holder of claim 11, wherein said support strap comprises a first and second strap and said holder base include opposite outer ends, each end being adapted to removably receive said first and second straps for removably attaching said straps to said holder base.

14. The tube holder of claim 13, wherein said first and second straps include a loop fastener on one strap and a hook fastener on said other strap for engaging said loop fastener and attaching said straps to each other for securing said tube holder to a patient.

15. A tube holder for supporting and retaining a tracheostomy tube or an endotracheal tube of the type having a tube and tube support flange, an inner cannula for insertion into the tube and inner cannula locking means for securing the inner cannula to the tube, the tube holder comprising a holder base having a body including a tube receiving opening adapted for receiving a barrel of a tube therethrough and further including a through-slot extending outward from and adjacent to the opening, the through-slot being adapted to prevent contact between an inner cannula locking means and the holder base for allowing the secure connection of an inner cannula to a tube and further including a removable, resilient member extending into the tube receiving opening for providing a snug fit for a tracheostomy tube.

16. The tube holder of claim 15, wherein the removable, resilient member is a perforated tab for easy for removal of the tab during tracheostomy insertion.

\* \* \* \* \*